(12) United States Patent
Westedt et al.

(10) Patent No.: US 8,337,733 B2
(45) Date of Patent: Dec. 25, 2012

(54) PREPARATION OF COMPOSITIONS WITH ESSENTIALLY NONCRYSTALLINE EMBEDDED MACROLIDE ANTIBIOTICS

(75) Inventors: Ulrich Westedt, Schriesheim (DE); Jörg Rosenberg, Ellerstadt (DE); Martin Knobloch, Neuhofen (DE); Norbert Steiger, Lingenfeld (DE); Harald Hach, Oberotterbach (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 45 days.

(21) Appl. No.: 12/673,230

(22) PCT Filed: Aug. 14, 2008

(86) PCT No.: PCT/EP2008/060706
§ 371 (c)(1),
(2), (4) Date: Aug. 26, 2010

(87) PCT Pub. No.: WO2009/024535
PCT Pub. Date: Feb. 26, 2009

(65) Prior Publication Data
US 2012/0001361 A1    Jan. 5, 2012

(30) Foreign Application Priority Data
Aug. 17, 2007 (EP) .................................. 07114569

(51) Int. Cl.
*B29C 47/00* (2006.01)
(52) U.S. Cl. .................................................. 264/176.1
(58) Field of Classification Search ............... 264/176.1
See application file for complete search history.

(56) References Cited

U.S. PATENT DOCUMENTS

| | | | |
|---|---|---|---|
| 5,844,105 A | 12/1998 | Liu et al. | |
| 5,858,986 A | 1/1999 | Liu et al. | |
| 5,945,405 A | 8/1999 | Spanton et al. | |
| 5,958,888 A * | 9/1999 | Macy et al. | 514/29 |
| 6,444,796 B1 | 9/2002 | Suh et al. | |
| 6,515,116 B2 | 2/2003 | Suh et al. | |
| 6,599,884 B2 | 7/2003 | Avrutov et al. | |

(Continued)

FOREIGN PATENT DOCUMENTS
EP          0852140 A1     7/1998
(Continued)

OTHER PUBLICATIONS

PCT/ISA/237, WO, Oct. 13, 2008, Written Opinion for PCT/EP2008/060706.

(Continued)

*Primary Examiner* — Larry Thrower
(74) *Attorney, Agent, or Firm* — Edwards Wildman Palmer LLP; Peter C. Lauro, Esq.; Weiying Yang, Esq.

(57) ABSTRACT

A description is given of a process for the preparation of a pharmaceutical composition of a macrolide antibiotic in essentially noncrystalline form, in which the macrolide antibiotic, a water-swellable polymer and a proton donor are blended in an extruder in the presence of water and forced through a die, the ratio by weight of the sum of macrolide antibiotic, water-swellable polymer and proton donor to water being at least 1:1. The macrolide antibiotic is preferably clarithromycin and the water-swellable polymer is preferably chosen from crosslinked polyvinylpyrrolidone, crosslinked sodium carboxymethylcellulose and crosslinked polyacrylic acid.

19 Claims, 11 Drawing Sheets

U.S. PATENT DOCUMENTS 6,627,743 B1 9/2003 Liu et al.
2003/0091627 A1* 5/2003 Sharma .................. 424/465

FOREIGN PATENT DOCUMENTS

WO 97/16174 A1 5/1997
WO 00/77017 A1 12/2000

OTHER PUBLICATIONS

PCT/ISA/210, WO, Oct. 13, 2008, International Search Report for PCT/EP2008/060706.
Yonemochi, et al., "Physicochemical properties of amorphous clarithromycin obtained by grinding and spray drying", European Jour. of Pharm. Sci,(7) 331-338, 1999.

* cited by examiner

FIG. 20

PREPARATION OF COMPOSITIONS WITH ESSENTIALLY NONCRYSTALLINE EMBEDDED MACROLIDE ANTIBIOTICS

RELATED APPLICATION

This application is the U.S. national phase, pursuant to 35 U.S.C. §371, of PCT international application Ser. No. PCT/EP2008/060706, filed Aug. 14, 2008, designating the United States and published in English on Feb. 26, 2009 as publication WO 2009/024535 A1, which claims priority to European application Ser. No. 07114569.2, filed Aug. 17, 2007. The entire contents of the aforementioned patent applications are incorporated herein by this reference.

The present invention relates to a process for the preparation of pharmaceutical compositions in which an essentially noncrystalline macrolide antibiotic is present.

Macrolide antibiotics are of importance in medicine as antimicrobial agents against a broad spectrum of gram-positive bacteria and mycoplasma. Various macrolide antibiotics have been described hitherto, e.g. erythromycin, oleandomycin, spiramycin, josamycin, roxithromycin, azithromycin, midecamycin and clarithromycin, which are used clinically, and tylosin, which finds application in the veterinary field.

The macrolide antibiotic 6-O-methylerythromycin A (clarithromycin) is of particular use in the treatment of common pediatric infections of the middle ear and of the upper respiratory tract.

The antibacterial action is based on inhibition of the intracellular protein synthesis of sensitive bacteria. The antibiotic selectively binds to the 50 S subunits of the bacterial ribosomes and thus prevents the translocation of activated amino acids. Clarithromycin shows a high in vitro and in vivo effectiveness against both reference bacteria and clinical isolates.

Five polymorphic forms (I, II, 0, III, IV) of clarithromycin are known up to now. The polymorphs and the preparation thereof are described in the patents U.S. Pat. Nos. 5,858,986, 5,844,105, 5,945,405, 6,627,743, 6,599,884, 6,515,116 and 6,444,796. Modification II is the thermodynamically more stable form in comparison with form I and is used commercially. Modification 0 is a solvate form of clarithromycin. The modification includes the solvate of ethanol, isopropanol, isopropyl acetate and tetrahydrofuran. Form III is an acetonitrile solvate of clarithromycin.

Amorphous clarithromycin is disclosed in WO 00/77017 and Eur. J. Pharm. Sci., 7 (1999), 331-338. The preparation is achieved both by spray drying an organic solution comprising the active substance and by milling the active substance.

EP 0 852 140 describes a process for the conversion into the amorphous state of a crystalline active substance in the presence of an auxiliary which induces the amorphous state and a substance which stabilizes the amorphous state.

A granulation process for clarithromycin is known from WO 97/16174. The active substance is granulated in a batch process together with a carbomer with the addition of water. The process comprises a double drying stage.

It was an object of the present invention to make available a continuous process for the preparation of pharmaceutical compositions comprising macrolide antibiotics in which the macrolide antibiotic is present in essentially noncrystalline form. The process should essentially dispense with the organic solvents known from the state of the art or should simplify the process known from WO 97/16174 by shortening the processing times and reducing the amount of water necessary for the granulation and accordingly reducing the drying cost.

A process has correspondingly been found in which the macrolide antibiotic, a water-swellable polymer and a proton donor are blended in an extruder in the presence of water and forced through a die, the ratio by weight of the sum of macrolide antibiotic, water-swellable polymer and proton donor to water being at least 1:1.

Use may be made, as extruder, of single-screw machines, intermeshing screw machines or even multi-screw extruders, in particular twin-screw extruders, which are corotating or counterrotating and, if appropriate, equipped with kneading disks. Corotating twin-screw extruders are particularly preferred. In this connection, the mixture is blended and densified by the screws in the extruder barrel and is conveyed by them to the outlet of the extruder, where it is forced through a die.

The composition obtained according to the process can subsequently be subjected to a drying stage. Different processes, such as, for example, drying in a drying cupboard and freeze drying, are possible for this. After the drying, the extrudate can then be further processed to give any dosage form.

In preferred embodiments, the macrolide antibiotic comprises 50 to 80% by weight of the sum of macrolide antibiotic, water-swellable polymer and proton donor. Particularly preferably, the macrolide antibiotic comprises 60 to 80% by weight of the sum of macrolide antibiotic, water-swellable polymer and proton donor.

The term "essentially noncrystalline" means, within the meaning of this invention, that not more than 5%, preferably not more than 2%, of the macrolide antibiotic is present in crystalline form. Compositions which are free from crystalline active substance are particularly preferred. Thus, the macrolide antibiotic can be present in the composition distributed in molecular disperse form or can comprise amorphous agglomerates homogeneously dispersed in the polymer matrix, the size of such agglomerates preferably lying in the range of less than or equal to 1 μm.

The term "macrolide antibiotic" is to be understood as meaning compounds according to the invention which comprise a lactone ring with 14-16 ring members to which two sugar molecules are bonded via oxygen linkages. Azithromycin, clarithromycin, dirithromycin, erythromycin, flurithromycin, josamycin, kitasamycin, midecamycin, miocamycin, oleandomycin, rokitamycin, rosaramycin, roxithromycin, spiramycin and tylosin or mixtures thereof may be understood here by way of example. Clarithromycin, roxithromycin, erythromycin and azithromycin are preferred and clarithromycin is particularly preferred.

The water-swellable polymer is preferably a crosslinked polymer. Crosslinked polyvinylpyrrolidone (e.g., Kollidon CL, BASF), crosslinked sodium carboxymethylcellulose (e.g., AcDiSol, FMC) and crosslinked polyacrylic acid (e.g., Carbopol, Noveon) are particularly preferred. Mixtures of the abovementioned polymers can also be used. The water-swellable polymer preferably has a water absorption capacity of at least 3.5 g of water per gram of polymer. Water absorption capacity within the meaning of the invention denotes the maximum amount of water which the polymer is able to bind so firmly that it cannot be separated from the polymer even by centrifuging. The water absorption capacity is determined by adding 40 ml of deionized water (pH 7) to 2 g of polymer in a 100 ml centrifuge tube and afterwards vigorously shaking the centrifuge tube for long enough for a suspension to be formed. The shaking is repeated after 5 and 10 minutes. Subsequently, the centrifuge tube is centrifuged at 2000 rpm for 15 minutes. After decanting the supernatant liquid from the centrifuge tube, the remaining residue is weighed. The ratio of weight of the polymer after hydration has been carried out to starting weight subsequently makes it possible to determine the water absorption capacity of the respective polymer.

In the process according to the invention at least one proton donor is used. Useful proton donors are selected from compounds having a pKa value less than 10, preferably less than 7. The water-swellable polymer can itself operate as proton donor if it comprises acid groups, such as carboxyl and/or sulfonyl groups, as is the case with the crosslinked polyacrylic acids. When neutral water-swellable polymers are used, the addition of an additional proton source is necessary. In this connection, organic acids, e.g. carboxylic acids and/or sulfonic acids, are preferred. Lactic acid, glycolic acid and citric acid are particularly suitable, lactic acid being particularly preferred. The molar ratio of acid to active substance generally lies between 0.9:1 and 1.5:1, preferably at approximately 1:1. With a lower acid content, it is not possible, under the processing conditions, to embed the active substance in the polymer matrix to a sufficient extent in molecularly disperse form or amorphously. Higher acid contents attract negative attention by an increase in decomposition products.

The addition of water is likewise necessary according to the process. The ratio by weight of active substance, polymer and acid to water is from 1:1 to 2.7:1. Without addition of water, the active substance is recovered distributed in crystalline form in the polymer (or it would be necessary to choose far higher extrusion temperatures, which, however, results in a considerable proportion of decomposition products with the active substance).

Since both the presence of water and of acid are essential for the macrolide antibiotic to be embedded in the polymer matrix in molecularly disperse form or amorphously, it is assumed that, by protonation of the active substance, its solubility in water increases and the dissolved active substance diffuses into the water-swellable polymer. This hypothesis is supported because the use of nonswellable polymers, such as are represented by the cation exchangers Amberlite IR 120 and Dowex 50WX8, together with water and crystalline active substance, shows after extrusion an unchanged morphology with regard to the crystalline active substance used.

The residence time of the material in the extruder is preferably less than 5 minutes, in particular less than 3 minutes. The extrusion temperatures generally lie between 40 and 80° C.

The extrusion temperature is preferably at least 40° C. if the ratio by weight of the sum of the macrolide antibiotic, water-swellable polymer and, if appropriate, proton donor to water is from 1.5:1 up to less than 1.9:1. If the ratio by weight is 1.9:1 or greater, the extrusion temperature is preferably at least 50° C.

The charging of the extruder is carried out continuously in a conventional way. The powder blend is preferably fed in freely, e.g. via a differential weigh feeder.

Different zones can be distinguished in the extruder. In the feed/conveying zone, the material is fed and conveyed essentially unchanged as powder/granules through use of conveying elements in the extruder. In the mixing zone, the material is homogenized; kneading blocks, left-hand thread and mixing elements or also combinations of the screw flights mentioned are used for this. A devolatilizing zone, in which a vacuum of 10-600 mbar (absolute pressure) is applied, optionally follows after this. The amount of material in the screw channel is increased in the compression and metering zone, which is achieved by use of elements with increasing degree of pitch, and the material is finally pressed through the die.

The addition of the water can take place at least partially into a powder blend of macrolide antibiotics and water-swellable polymer and, if appropriate, proton donor before feeding to the extruder. However, it is also possible to incorporate the water in the blend at least partially inside the extruder, preferably in the conveying or mixing zone. In this connection, the addition of the water is advisably carried out using a metering pump. Optionally, the proton source can be incorporated dissolved in the water for the mixing.

In a preferred embodiment, the water added is at least partially and preferably largely removed by application of vacuum to a devolatilizing unit situated between mixing zone and compression zone. A vacuum of 10-600 mbar, preferably 30-200 mbar, particularly preferably 50-150 mbar, is advisably applied. Through this processing action, the time necessary for the drying of the extrudate can be reduced or this possibly makes the drying stage completely superfluous. The drying is carried out in the drying cupboard or under vacuum up to constant weight, i.e. until the residual water content in the extrudate is less than 2%.

After the drying stage, the composition obtained can be further processed to give different dosage forms. The term "dosage forms" is understood to mean all forms which are suitable for use as medicaments, in particular for oral administration, and animal feed. These include, for example, tablets of any form, pellets or granules. These furthermore include forms such as films, implants and suppositories.

The compositions can subsequently also be milled to give a powder and can then be conventionally compressed to give tablets. In this connection, tableting auxiliaries, such as colloidal silica, calcium hydrogen phosphate, lactose, microcrystalline cellulose, starch or magnesium stearate, can be used in conjunction.

In particular, the powders and granules, because of the noncrystallinity of the active substance, do not show, in the tableting, the tendency toward adhesion to the tableting punch observable with macrolide antibiotics and in particular with clarithromycin and considerably simplify the tableting process for the macrolide antibiotics.

Because of the noncrystallinity of the active substance, the compositions show an increased bioavailability with simultaneously good stability on storage.

The invention is more fully illustrated from the figures and by the following examples. The X-ray diffraction diagrams were recorded with a D-5005 diffractometer from Siemens, Germany, radiation source type KFL Cu 2K.

EXAMPLE 1

A powder blend of 69% by weight of clarithromycin and 20% by weight of crosscarmellose sodium (AcDiSol, type A, FMC Corp., Newark, USA) was processed with a throughput of 180 g/h in a twin-screw extruder (Haake Rheomex PTW 16 from Thermo Electron) at an extrusion temperature of 50° C. to give a homogeneous material. A 10% lactic acid solution was metered into the material in the extruder at 224 g/h, corresponding to 11% by weight of lactic acid in the dry extrudate material. Extrusion was carried out with a torque of 30-50 Nm at a screw speed of 30. Wet but flowable granules were obtained and were dried in a hot air dryer at 50° C. for 25 minutes. No crystalline active substance could be detected in the product.

Figure 1:
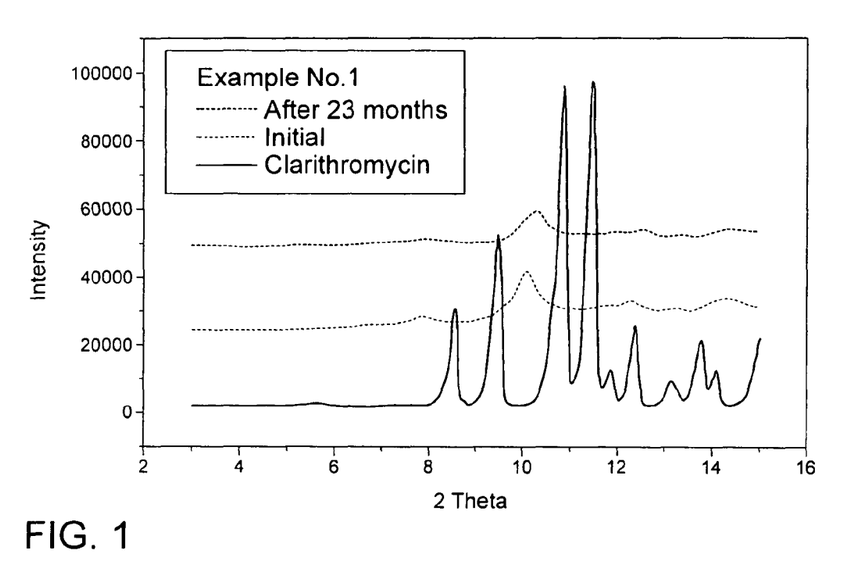

FIG. 1 shows the X-ray diffraction diagram of the product obtained.

EXAMPLE 2

A powder blend of 65% by weight of clarithromycin and 27% by weight of crosscarmellose sodium (AcDiSol, type A, FMC Corp., Newark, USA) was processed with a throughput of 184 g/h in a twin-screw extruder (Haake Rheomex PTW 16 from Thermo Electron) at an extrusion temperature of 50° C. to give a homogeneous material. A 16% lactic acid solution was metered into the material in the extruder at 96 g/h, corresponding to 8% by weight of lactic acid in the dry extrudate material. Extrusion was carried out with a torque of 30-50 Nm at a screw speed of 30. Wet but flowable granules were obtained and were dried in a hot air dryer at 50° C. for 25 minutes. No crystalline active substance could be detected in the product.

Figure 2:
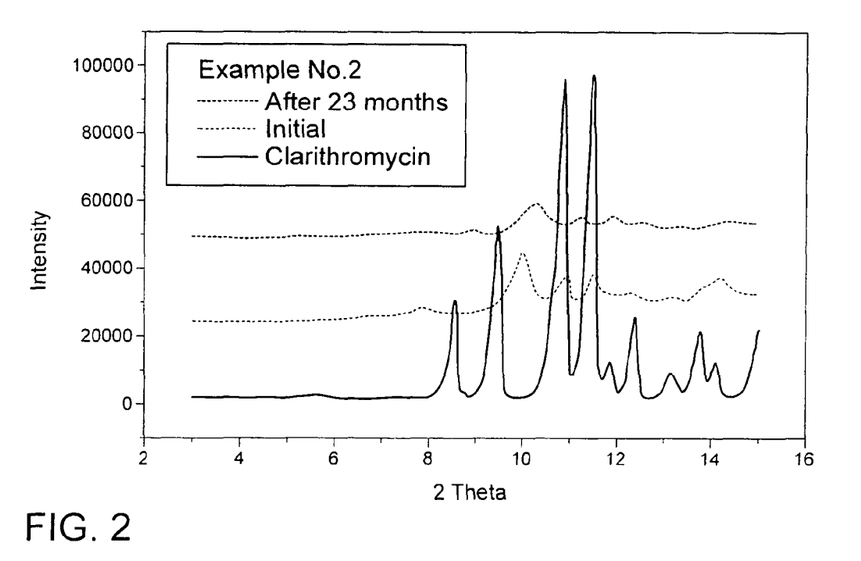

FIG. 2 shows the X-ray diffraction diagram of the product obtained.

EXAMPLE 3

A powder blend of 69% by weight of clarithromycin and 20% by weight of crospovidone (Kollidon CL M, BASF, Ludwigshafen, Germany) was processed with a throughput of 180 g/h in a twin-screw extruder (Haake Rheomex PTW 16 from Thermo Electron) at an extrusion temperature of 50° C. to give a homogeneous material. A 10% lactic acid solution was metered into the material in the extruder at 224 g/h, corresponding to 11% by weight of lactic acid in the dry extrudate material. Extrusion was carried out with a torque of 30-50 Nm at a screw speed of 30. Wet but flowable granules were obtained and were dried in a hot air dryer at 50° C. for at least 25 minutes. No crystalline active substance could be detected in the product.

Figure 3:
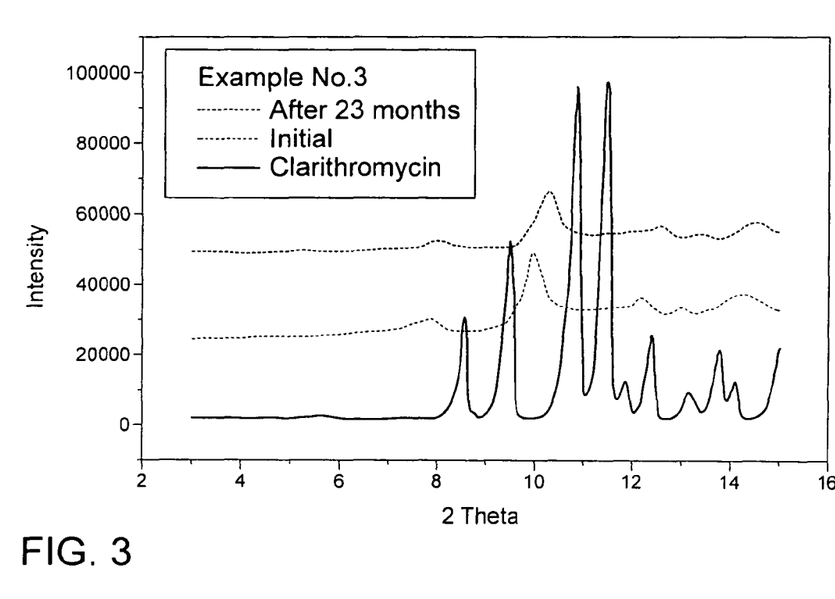

FIG. 3 shows the X-ray diffraction diagram of the product obtained.

EXAMPLE 4

A powder blend of 63% by weight of clarithromycin and 37% by weight of Carbopol 974P NF was processed with a throughput of 588 g/h in a twin-screw extruder (Haake Rheomex PTW 16 from Thermo Electron) at an extrusion temperature of 50° C. to give a homogeneous material. 156 g/h of water were metered into the material in the extruder. Extrusion was carried out with a torque of 30-50 Nm at a screw speed of 30. Wet but flowable granules were obtained and were dried in a hot air dryer at 50° C. for at least 25 minutes. No crystalline active substance could be detected in the product.

Figure 4:
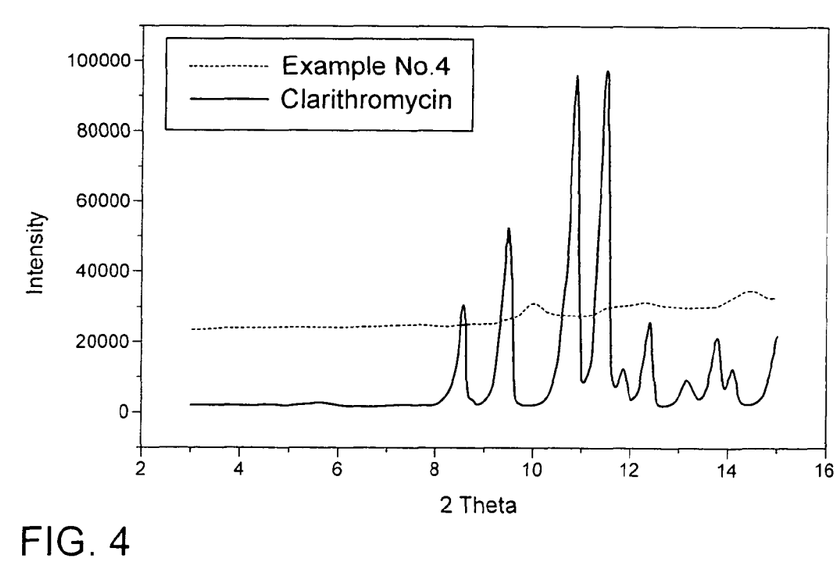

FIG. 4 shows the X-ray diffraction diagram of the product obtained.

EXAMPLE 5

A powder blend of 70% by weight of clarithromycin and 30% by weight of Carbopol 974P NF was processed with a throughput of 342 g/h in a twin-screw extruder (Haake Rheomex PTW 16 from Thermo Electron) at an extrusion temperature of 22° C. 160 g/h of water were metered into the material in the extruder. Extrusion was carried out with a torque of 80-100 Nm at a screw speed of 20. White wet flowable granules were obtained and were dried in a hot air dryer at 50° C. for at least 25 minutes. No crystalline active substance could be detected in the product.

Figure 5:
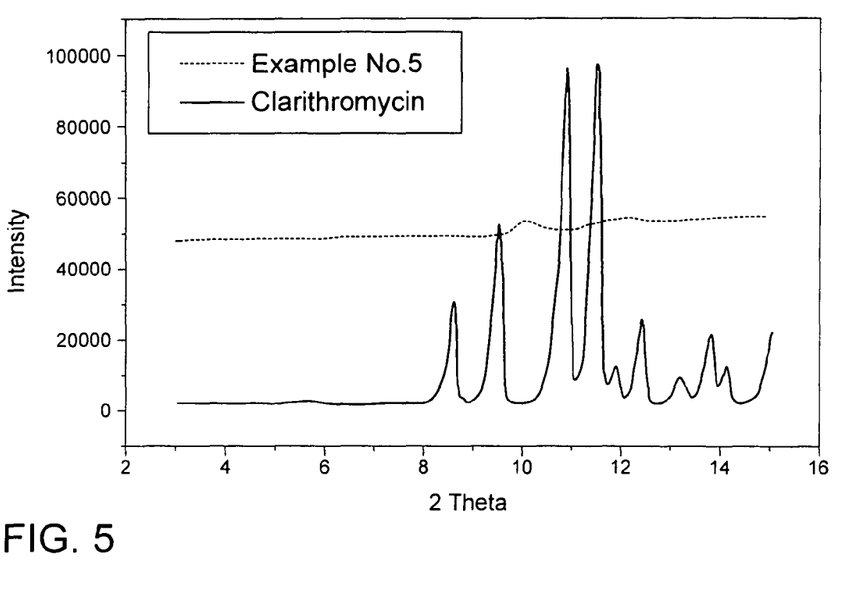

FIG. 5 shows the X-ray diffraction diagram of the product obtained.

EXAMPLE 6

A powder blend of 80% by weight of clarithromycin and 20% by weight of Carbopol 974P NF was processed with a throughput of 180 g/h in a twin-screw extruder (Haake Rheomex PTW 16 from Thermo Electron) at an extrusion temperature of 50° C. 90 g/h of water were metered into the material in the extruder. Extrusion was carried out with a torque of 20-40 Nm at a screw speed of 30. White wet flowable granules were obtained and were dried in a hot air dryer at 50° C. for at least 25 minutes. No crystalline active substance could be detected in the product.

Figure 6:
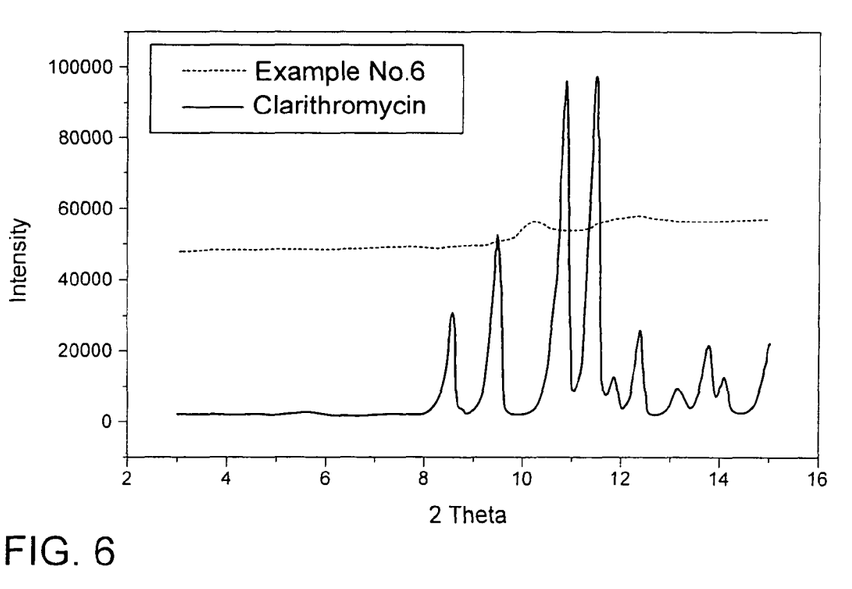

FIG. 6 shows the X-ray diffraction diagram of the product obtained.

COMPARATIVE EXAMPLE 7

A powder blend of 63% by weight of clarithromycin and 37% by weight of Amberlite IR 120 was processed with a throughput of 180 g/h in a twin-screw extruder (Haake Rheomex PTW 16 from Thermo Electron) at a temperature of 50° C. to give a homogeneous material. 180 g/h of water were metered into the material in the extruder. Extrusion was carried out with a torque of 30-50 Nm at a screw speed of 30. Wet nonflow-able granules were obtained and were dried in a hot air dryer at 50° C. for 25 minutes. Crystalline active substance could be detected in the product.

Figure 7:
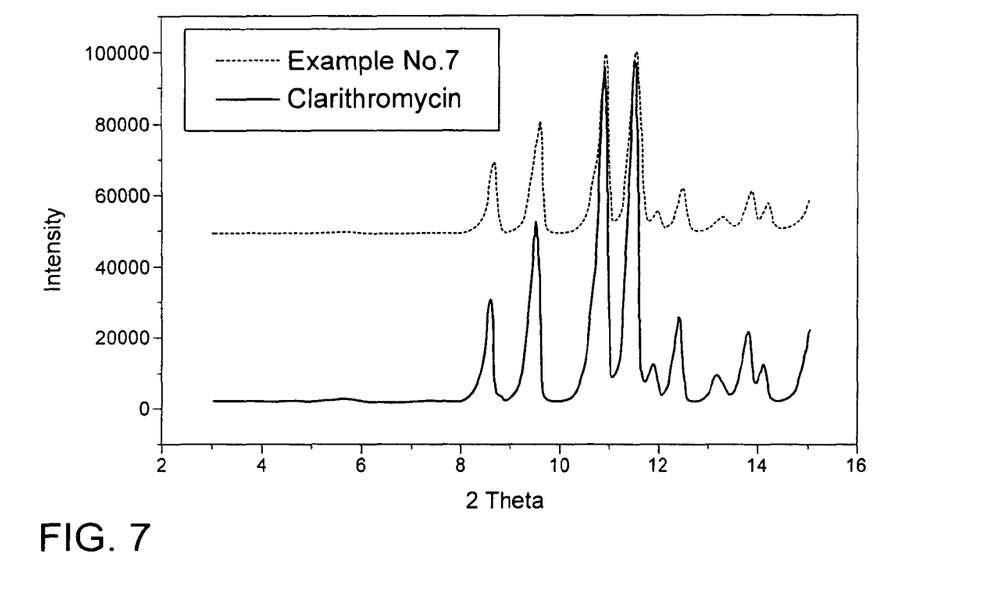

FIG. 7 shows the X-ray diffraction diagram of the product obtained.

COMPARATIVE EXAMPLE 8

A powder blend of 63% by weight of clarithromycin and 37% by weight of Dowex 50WX8 was processed with a throughput of 180 g/h in a twin-screw extruder (Haake Rheomex PTW 16 from Thermo Electron) at a temperature of 50° C. to give a homogeneous material. 180 g/h of water were metered into the material in the extruder. Extrusion was carried out with a torque of 30-50 Nm at a screw speed of 30. Wet nonflow-able granules were obtained and were dried in a hot air dryer at 50° C. for 25 minutes. Crystalline active substance could be detected in the product.

Figure 8:
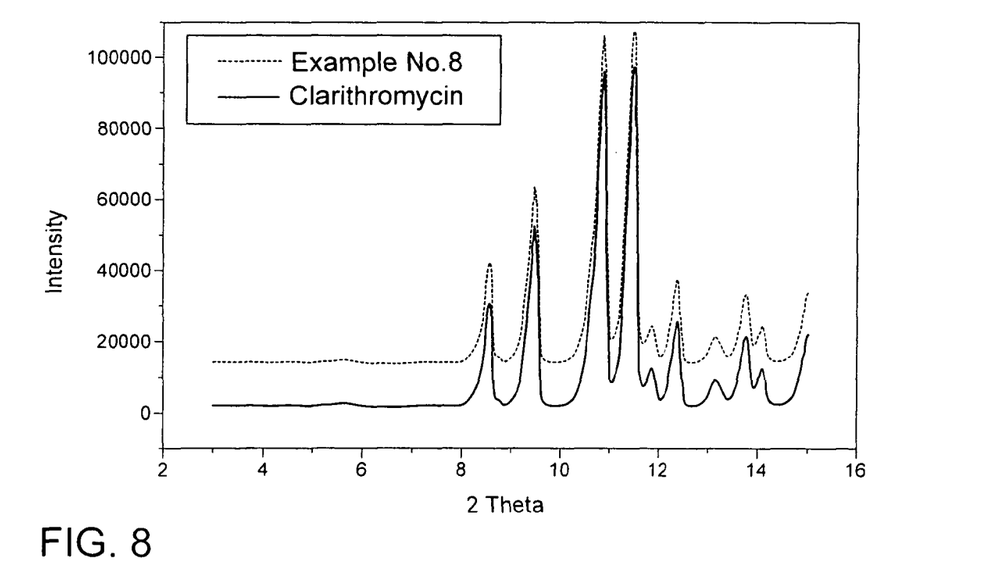

FIG. 8 shows the X-ray diffraction diagram of the product obtained.

COMPARATIVE EXAMPLE 9

A powder blend of 63% by weight of clarithromycin and 37% by weight of Eudragit L100-55 (Röhm) was processed with a throughput of 180 g/h in a twin-screw extruder (Haake Rheomex PTW 16 from Thermo Electron) at a temperature of 50° C. to give a homogeneous material. 180 g/h of water were metered into the material in the extruder. Extrusion was carried out with a torque of 30-50 Nm at a screw speed of 30. Wet sticky nonflowable granules were obtained and were dried in a hot air dryer at 50° C. for 25 minutes. Crystalline active substance could be detected in the product.

Figure 9:
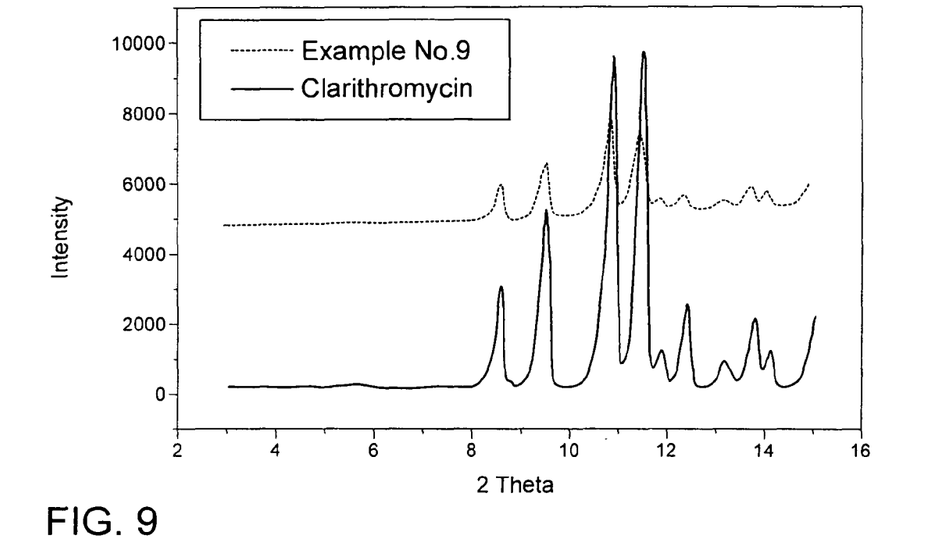

FIG. 9 shows the X-ray diffraction diagram of the product obtained.

COMPARATIVE EXAMPLE 10

A powder blend of 63% by weight of clarithromycin and 37% by weight of hydroxypropylmethylcellulose phthalate HPMCP (Shin-Etsu) was processed with a throughput of 180 g/h in a twin-screw extruder (Haake Rheomex PTW 16 from Thermo Electron) at a temperature of 50° C. to give a homogeneous material. 180 g/h of water were metered into the material in the extruder. Extrusion was carried out with a torque of 30-50 Nm at a screw speed of 30. Wet sticky nonflowable granules were obtained and were dried in a hot air dryer at 50° C. for 25 minutes. Crystalline active substance could be detected in the product.

Figure 10:
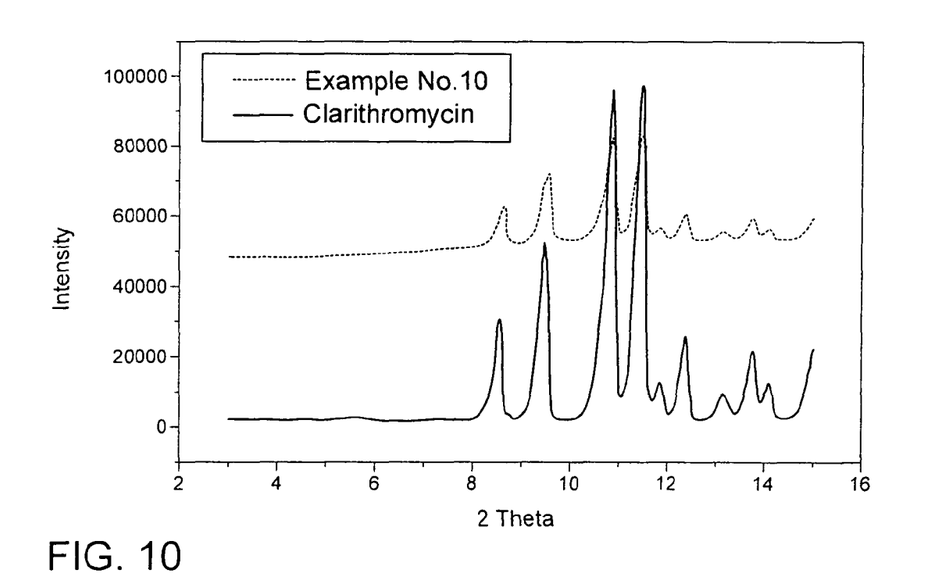

FIG. 10 shows the X-ray diffraction diagram of the product obtained.

COMPARATIVE EXAMPLE 11

A powder blend of 63% by weight of clarithromycin and 37% by weight of hydroxypropylmethylcellulose acetate succinate HPMCAS (Shin-Etsu) was processed with a throughput of 180 g/h in a twin-screw extruder (Haake Rheomex PTW 16 from Thermo Electron) at a temperature of 50° C. to give a homogeneous material. 180 g/h of water were metered into the material. Extrusion was carried out with a torque of 30-50 Nm at a screw speed of 30. Wet, slightly sticky, nonflowable granules were obtained and were dried in a hot air dryer at 50° C. for 25 minutes. Crystalline active substance could be detected in the product.

Figure 11:
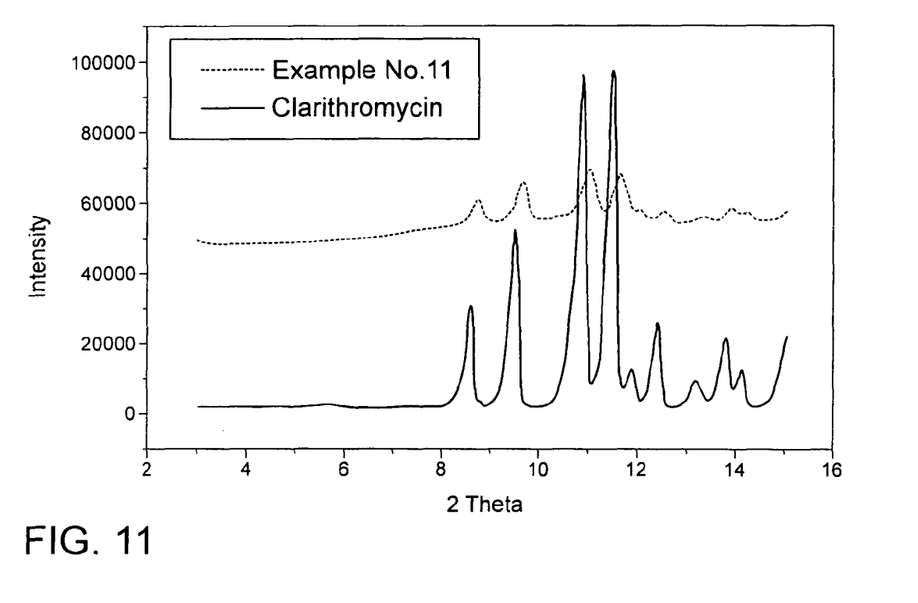

FIG. 11 shows the X-ray diffraction diagram of the product obtained.

COMPARATIVE EXAMPLE 12

A powder blend of 63% by weight of clarithromycin and 29.3% by weight of sodium alginate LF 240 D was processed with a throughput of 184 g/h in a twin-screw extruder (Haake Rheomex PTW 16 from Thermo Electron) at an extrusion temperature of 50° C. to give a homogeneous material. A 16% lactic acid solution was metered into the material in the extruder at 96 g/h, corresponding to 8% by weight of lactic acid in the dry extrudate material. Extrusion was carried out with a torque of 30-50 Nm at a screw speed of 30. Wet, slightly sticky, nonflowable granules were obtained and were dried in a hot air dryer at 50° C. for 25 minutes. Crystalline active substance could be detected in the product.

Figure 12:
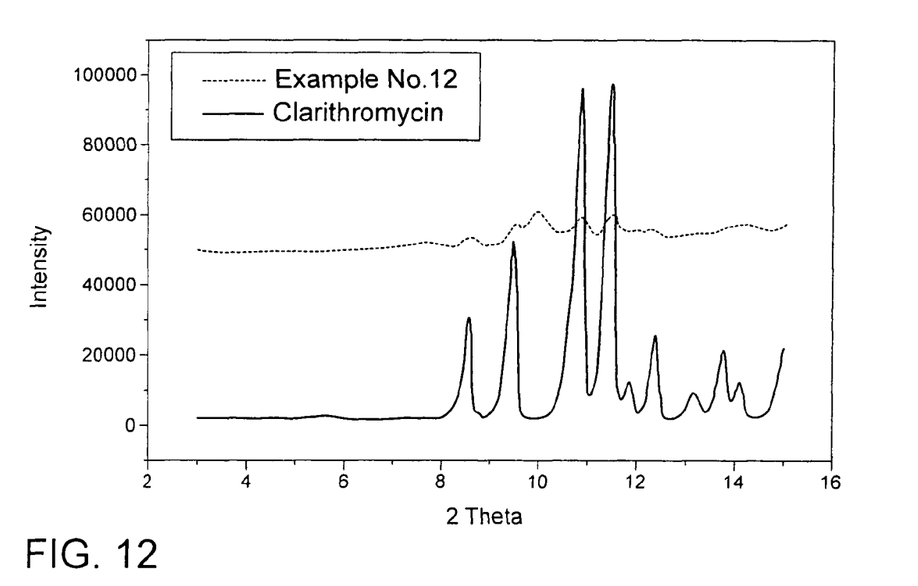

FIG. 12 shows the X-ray diffraction diagram of the product obtained.

COMPARATIVE EXAMPLE 13

A powder blend of 63% by weight of clarithromycin and 29.3% by weight of hydroxypropylmethylcellulose Methocel K100 (Aqualon) was processed with a throughput of 184 g/h in a twin-screw extruder (Haake Rheomex PTW 16 from Thermo Electron) at an extrusion temperature of 50° C. to give a homogeneous material. A 16% lactic acid solution was metered into the material in the extruder at 96 g/h, corresponding to 8% by weight of lactic acid in the dry extrudate material. Extrusion was carried out with a torque of 30-50 Nm at a screw speed of 30. Wet nonflowable granules were obtained and were dried in a hot air dryer at 50° C. for 25 minutes. Crystalline active substance could be detected in the product.

Figure 13:
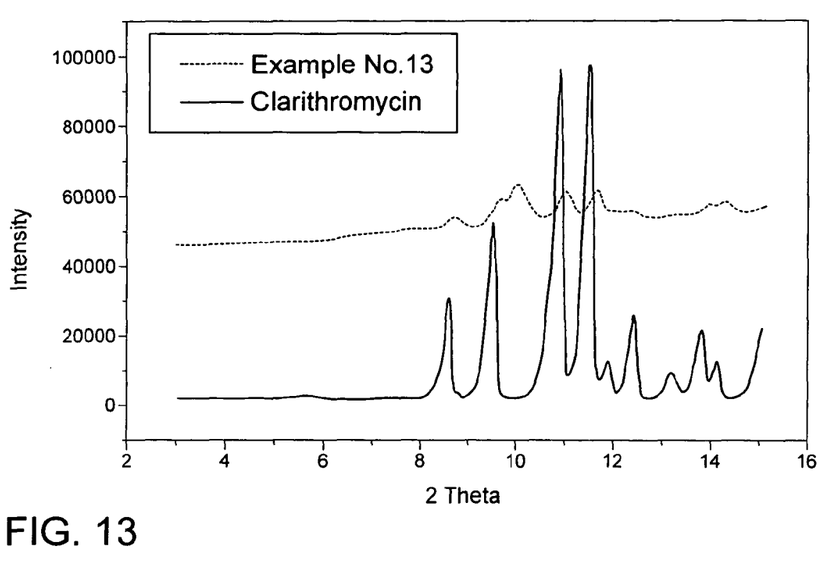

FIG. 13 shows the X-ray diffraction diagram of the product obtained.

COMPARATIVE EXAMPLE 14

A powder blend of 63% by weight of clarithromycin and 29.3% by weight of corn starch was processed with a throughput of 184 g/h in a twin-screw extruder (Haake Rheomex PTW 16 from Thermo Electron) at an extrusion temperature of 50° C. to give a homogeneous material. A 16% lactic acid solution was metered into the material in the extruder at 96 g/h, corresponding to 8% by weight of lactic acid in the dry extrudate material. Extrusion was carried out with a torque of 30-50 Nm at a screw speed of 30. Wet but flowable granules were obtained and were dried in a hot air dryer at 50° C. for 25 minutes. Crystalline active substance could be detected in the product.

Figure 14:
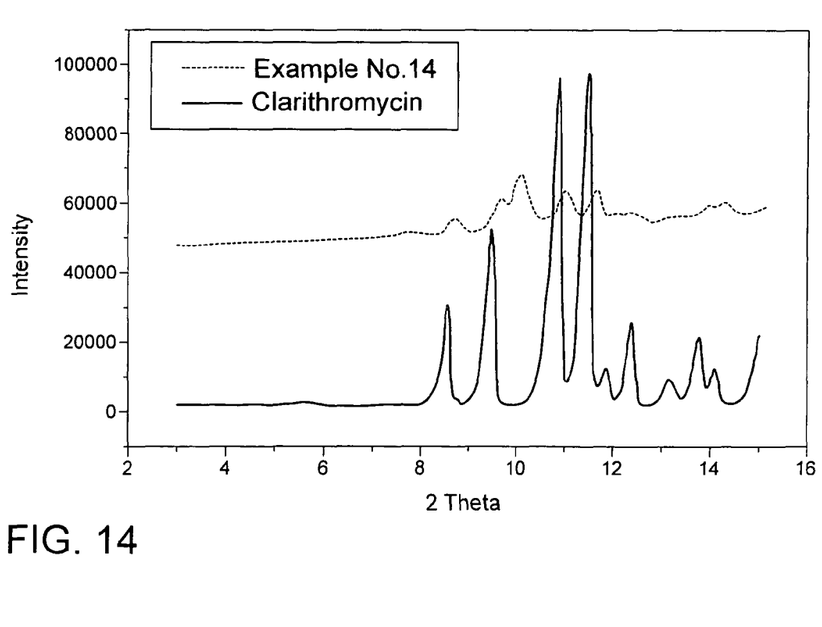

FIG. 14 shows the X-ray diffraction diagram of the product obtained.

Influence of the Reaction Temperature

COMPARATIVE EXAMPLE 15

A powder blend of 63% by weight of clarithromycin and 37% by weight of Carbopol 974P NF was processed with a throughput of 254 g/h in a twin-screw extruder (Haake Rheomex PTW 16 from Thermo Electron) at an extrusion temperature of 22° C. to give a homogeneous material. 164 g/h of water were metered into the material in the extruder. Extrusion was carried out with a torque of 25 Nm at a screw speed of 20. Wet but flowable granules were obtained and were dried in a hot air dryer at 50° C. for 25 minutes. Small amounts of crystalline active substance were detected in the product.

Figure 15A:
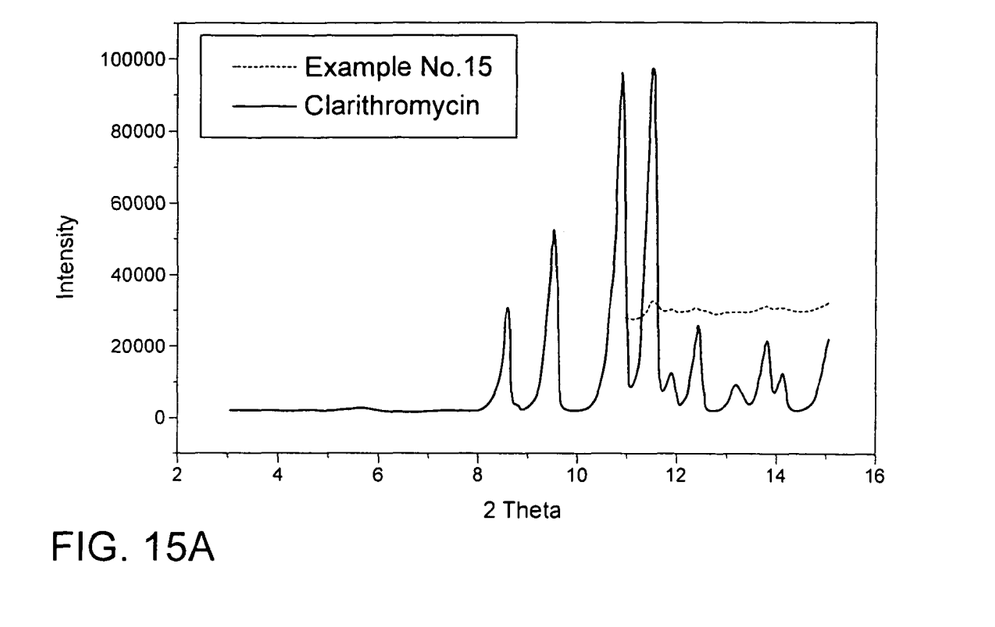

FIG. 15a shows the X-ray diffraction diagram of the product obtained.

Figure 15B:
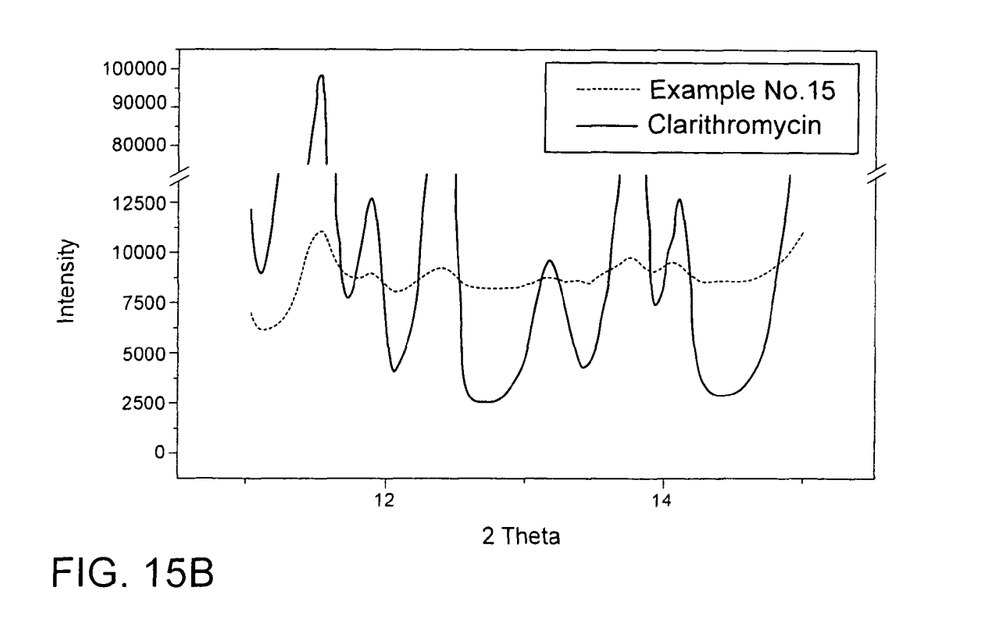

FIG. 15b shows a partial cutout of the X-ray diffraction diagram from FIG. 15a in magnification.

EXAMPLE 16

A powder blend of 63% by weight of clarithromycin and 37% by weight of Carbopol 974P NF was processed with a throughput of 254 g/h in a twin-screw extruder (Haake Rheomex PTW 16 from Thermo Electron) at an extrusion temperature of 70° C. to give a homogeneous material. 164 g/h of water were metered into the material in the extruder. Extrusion was carried out with a torque of 100 Nm at a screw speed of 30. Wet flow-able granules were obtained and were dried in a hot air dryer at 50° C. for at least 25 minutes. No crystalline active substance could be detected in the product.

Figure 16:
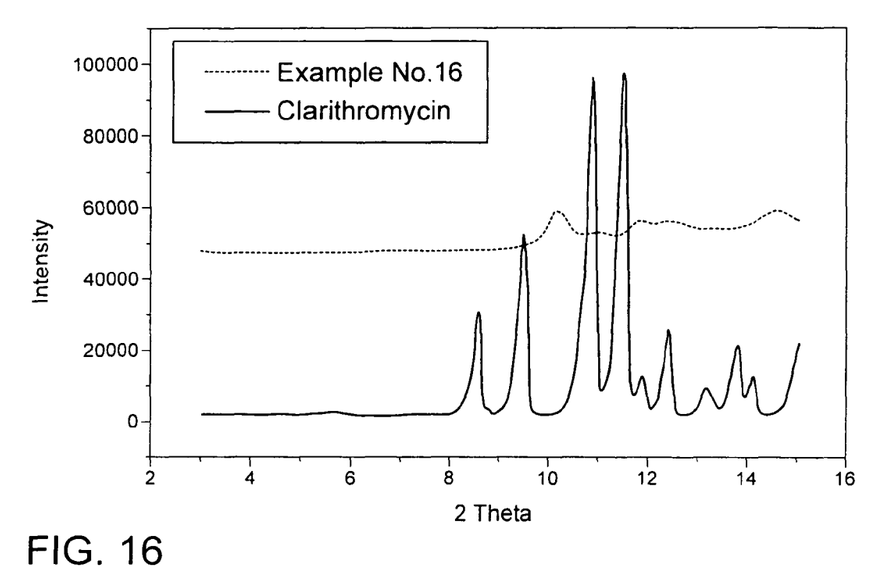

FIG. 16 shows the X-ray diffraction diagram of the product obtained.

Influence of the Water Content

EXAMPLE 17

A powder blend of 80% by weight of clarithromycin and 20% by weight of Carbopol 974P NF was processed with a throughput of 150 g/h in a twin-screw extruder (Haake Rheomex PTW 16 from Thermo Electron) at an extrusion temperature of 22° C. to give a homogeneous material. 150 g/h of water were metered into the material in the extruder. Extrusion was carried out with a torque of 1-9 Nm at a screw speed of 20. Very wet but still flowable granules were obtained and were dried in a hot air dryer at 50° C. for at least 25 minutes. No crystalline active substance could be detected in the product.

Figure 17:
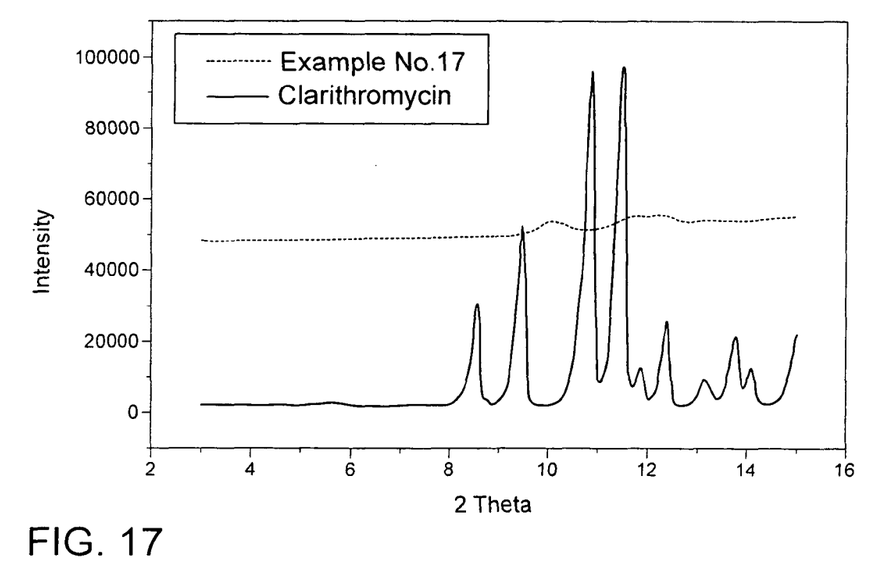

FIG. 17 shows the X-ray diffraction diagram of the product obtained.

COMPARATIVE EXAMPLE 18

A powder blend of 80% by weight of clarithromycin and 20% by weight of Carbopol 974P NF was processed with a throughput of 300 g/h in a twin-screw extruder (Haake Rheomex PTW 16 from Thermo Electron) at an extrusion temperature of 22° C. to give a homogeneous material. 150 g/h of water were metered into the material in the extruder. Extrusion was carried out with a torque of 20-40 Nm at a screw speed of 20. Very wet but still flowable granules were obtained and were dried in a hot air dryer at 50° C. for at least 25 minutes. Crystalline active substance could be detected in the product.

Figure 18A:
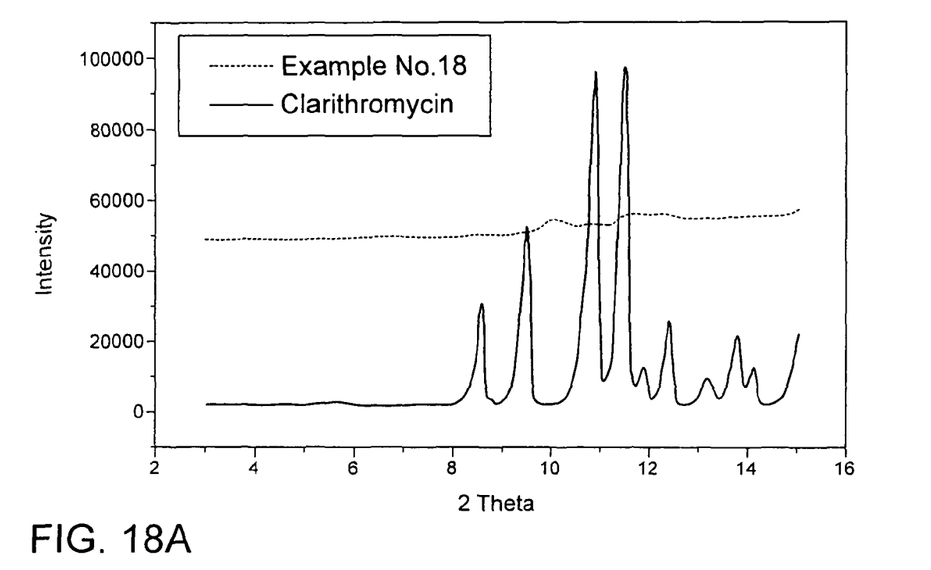

FIG. 18a shows the X-ray diffraction diagram of the product obtained.

Figure 18B:
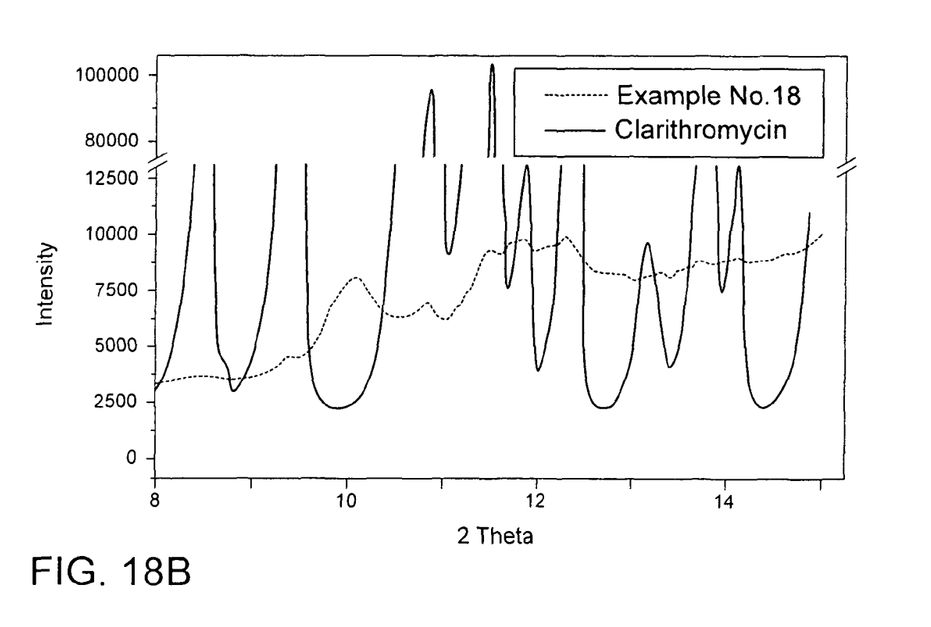

FIG. 18b shows a partial cutout of the X-ray diffraction diagram from FIG. 18a in magnification.

Variation in the Amount of Acid

EXAMPLE 19

A powder blend of clarithromycin and crosscarmellose sodium (AcDiSol, type A, FMC Corp., Newark, USA) in the ratio of 2.27:1 was processed with a throughput of 184 g/h in a twin-screw extruder (Haake Rheomex PTW 16 from Thermo Electron) at a temperature of 50° C. to give a homogeneous material. In order to achieve, with a ratio of solid to liquid of 2:1, a final content of 0, 0.77, 7.7 and 9.2% by weight of lactic acid in the dry extrudate material, 92 g/h of water or in each case 92 g/h of a 1.54%, 15.4% and 18.4% lactic acid solution were metered into the extruder. Extrusion was carried out with a torque of 30-50 Nm at a screw speed of 30. In each case, wet but flowable granules were obtained and were dried in a hot air dryer at 50° C. for 25 minutes. In this connection, a reduction in the active substance crystallinity could be detected in the product with increasing proportion of acid in the mixture.

Figure 19:
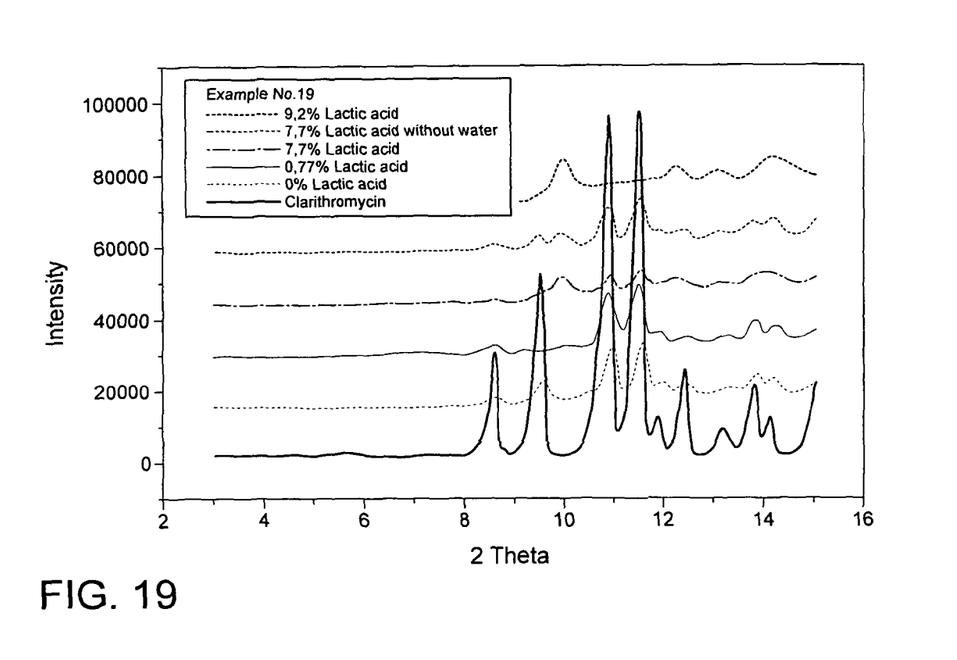

FIG. 19 shows the X-ray diffraction diagram of the product obtained.

EXAMPLE 20

A powder blend of clarithromycin and crospovidone (type Kollidon CL M, BASF) in the ratio of 2.27:1 was processed with a throughput of 184 g/h in a twin-screw extruder (Haake Rheomex PTW 16 from Thermo Electron) at a temperature of 50° C. to give a homogeneous material. In order to achieve, with a ratio of solid to liquid of 2:1, a final content of 0, 0.77, 7.7 and 9.2% by weight of lactic acid in the dry extrudate material, 92 g/h of water or in each case 92 g/h of a 1.54%, 15.4% and 18.4% lactic acid solution were metered into the extruder. Extrusion was carried out with a torque of 30-50 Nm at a screw speed of 30. In each case, wet but flowable granules were obtained and were dried in a hot air dryer at 50° C. for 25 minutes. In this connection, a reduction in the active substance crystallinity could be detected in the product with increasing proportion of acid in the mixture.

Figure 20:
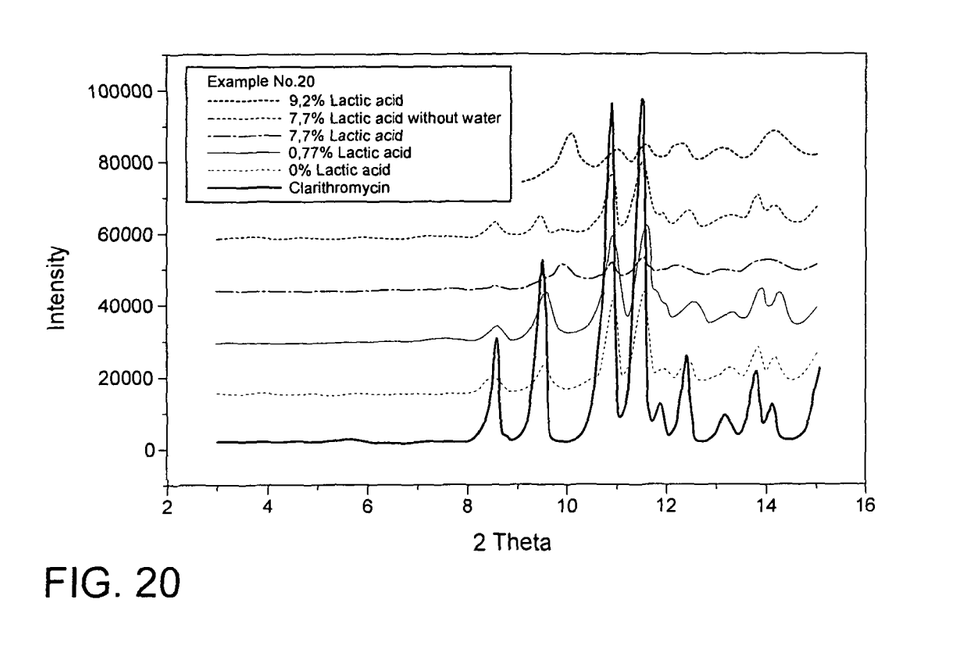

FIG. 20 shows the X-ray diffraction diagram of the product obtained.

What is claimed is:

1. A process for the preparation of a pharmaceutical composition of a macrolide antibiotic in essentially noncrystalline form, comprising
   mixing the macrolide antibiotic and a water-swellable polymer as a blend, wherein the mixing takes place in an extruder in the presence of water to obtain a mixture; and
   forcing the mixture through a die,
   wherein said water-swellable polymer is selected from crosslinked polyvinylpyrrolidone, crosslinked sodium carboxymethyl-cellulose, and crosslinked polyacrylic acid,
   provided that when the water-swellable polymer does not comprise crosslinked polyacrylic acid, the blend further comprises a proton donor that is mixed with the macrolide antibiotic and the water-swellable polymer;
   wherein the ratio by weight of the blend to water is at least 1:1.

2. The process as claimed in claim 1, wherein the macrolide antibiotic is present at 50% to 80% by weight of the blend.

3. The process as claimed in claim 2, wherein the macrolide antibiotic is present at 60% to 80% by weight of the blend.

4. The process as claimed in claim 1, wherein the macrolide antibiotic is present in molecular disperse form in the composition obtained.

5. The process as claimed in claim 1, wherein the macrolide antibiotic is present in amorphous form in the composition obtained.

6. The process as claimed in claim 1, wherein the macrolide antibiotic is selected from clarithromycin, roxithromycin, erythromycin and azithromycin.

7. The process as claimed in claim 6, wherein the macrolide antibiotic is clarithromycin.

8. The process as claimed in claim 1, wherein the water-swellable polymer has a water absorption capacity of at least 3.5 g of water/g of polymer.

9. The process as claimed in claim 1, wherein the proton donor is an organic acid.

10. The process as claimed in claim 9, wherein the organic acid is lactic acid, glycolic acid or citric acid.

11. The process as claimed in claim 9, wherein the organic acid is lactic acid.

12. The process as claimed in claim 1, wherein the ratio by weight of the blend to water is from 1:1 to 2.7:1.

13. The process as claimed in claim 1, wherein the water is added to the blend before the feeding of the blend to the extruder.

14. The process as claimed in claim 1, wherein the water is added to the blend at least partially in a conveying zone of the extruder.

15. The process as claimed in claim 1, wherein the mixture is extruded as a temperature in the range of between 40 and 80° C.

16. The process as claimed in claim 1, in which the mixture is subjected to a vacuum before the die in order to at least partially remove the water.

17. The process as claimed in claim 1, wherein the ratio by weight of the blend to water is from 1.5:1 up to less than 1.9:1, and the mixture is extruded at a temperature of 40°C. or higher.

18. The process as claimed in claim 1, wherein the extruder is a multi-screw extruder.

19. The process as claimed in claim 1, wherein the ratio by weight of the blend to water is 1.9:1 or greater, and the mixture is extruded at a temperature of 50° C. or higher.

* * * * *